United States Patent [19]
Umezawa

[11] Patent Number: 5,784,484
[45] Date of Patent: Jul. 21, 1998

[54] DEVICE FOR INSPECTING PRINTED WIRING BOARDS AT DIFFERENT RESOLUTIONS

[75] Inventor: Tadashi Umezawa, Tokyo, Japan

[73] Assignee: NEC Corporation, Tokyo, Japan

[21] Appl. No.: 625,222

[22] Filed: Apr. 1, 1996

[30] Foreign Application Priority Data

Mar. 30, 1995 [JP] Japan ............. 7-073112

[51] Int. Cl.$^6$ ................................ G06K 9/62
[52] U.S. Cl. ................................ 382/148
[58] Field of Search ................ 382/144, 145, 382/146, 147, 148, 149, 150, 151, 228, 299, 141, 112; 364/150, 468.17, 468.28, 554, 555; 348/87, 126, 237; 356/237, 394; 250/559.34, 559.45, 559.46, 559.47

[56] References Cited

U.S. PATENT DOCUMENTS

| | | | |
|---|---|---|---|
| 4,628,531 | 12/1986 | Okamoto et al. | 382/148 |
| 4,764,969 | 8/1988 | Ohtombe et al. | 382/148 |
| 5,150,423 | 9/1992 | Hoki | 382/8 |
| 5,625,703 | 4/1997 | Okuda et al. | 382/112 |

FOREIGN PATENT DOCUMENTS 4-69777  3/1992  Japan.

*Primary Examiner*—David K. Moore
*Assistant Examiner*—Brian P. Werner
*Attorney, Agent, or Firm*—Foley & Lardner

[57] ABSTRACT

A pattern inspecting device and associated inspection method are provided that appropriately adjust inspection resolution in accordance with the quality of printed boards under inspection, thereby enabling a reduction of the inspection time. The pattern inspecting device of the present invention is made up of a confirmation station and an optical inspection device section 1 that includes an image signal processor 3, an image analyzer 4, an inspection result processor 5, a CCD camera 6, a pair of illumination lamps 7, and an inspection table 8. The image signal processor 3 A/D converts the image data outputted by the camera, converts this signal to binary, and then to a digital image signal. The image analyzer 4 compares the digital image signal outputted by the image signal processor 3 with standard inspection data and outputs inspection results. The inspection result processor 5 statistically analyzes the inspection result data outputted by the image analyzer 4, selects a resolution appropriate to the analysis results, calculates standard inspection data according to this resolution, and sets the result as the next standard inspection data.

4 Claims, 2 Drawing Sheets

DEVICE FOR INSPECTING PRINTED WIRING BOARDS AT DIFFERENT RESOLUTIONS

BACKGROUND OF THE INVENTION

1. Field of the Invention

The present invention relates to a pattern inspecting device and its method, and particularly to a pattern inspecting device and method for use in inspecting the pattern of a printed wiring board.

2. Description of the Related Art

This type of pattern inspecting device and inspection method necessitates, as the first step in inspecting a printed wiring board, the preparation of master data for setting each parameter and comparing patterns in order to effect image recognition and determine approval or rejection of a printed wiring board. These master data are produced from image data obtained through automatic production from the original pattern image data of a board to be inspected, or from image data found from the boards to be inspected itself. In this way, the obtained pattern data and each parameter of the printed wiring board are registered as master data of the board to be inspected, and based on this master data, a design rule check (hereinafter abbreviated "DRC") as well as a comparative inspection are carried out for the board to be inspected and defects are extracted. When preparing the master data, the size of one pixel in image recognition, i.e., resolution, is set beforehand. Although the ability to detect minute defects in an inspected board increases with decrease in the set value for pixel size of this image recognition resolution, the amount of data also increases in reverse proportion to the pixel size, meaning that more time is required when inspecting a pattern for image processing, DRC, and comparative inspection processing, with the result that the process of detecting defects is considerably delayed.

Accordingly, in prior-art pattern inspecting devices and associated inspection methods, consideration is given to the inspection accuracy and inspection time of the printed wiring board when setting resolution to between 1/n-th and 1/(10n)-th of the standard pattern width of the board to be inspected, and in addition, this resolution is established as a fixed value. Moreover, new master data must be prepared when altering this resolution.

An example of a printed circuit board pattern inspecting device that shortens inspection time is described in Japanese Patent Laid-open No. 69777/92.

According to this inspection method, an edge of a printed board to be inspected is extracted using either a standard printed circuit board judged to be a good article or the mask film used for producing the printed circuit board that is to be inspected. Defects in the edge perimeter are extracted, while defects occurring outside the edge perimeter are deemed unimportant for purposes of quality control and are not extracted. In this way, by selecting a specific area and limiting the detection of defects to this area, the defect extraction processing time can be reduced and inspection time can be accordingly shortened.

In the above-described prior-art pattern inspecting device and method, resolution used in image recognition is set to a fixed value when preparing the master data, and as a result, the volume of image data corresponding to the size of resolution is set to a prescribed value, and consequently, the processing time necessary for image processing, DRC, and comparative inspection processing during pattern inspection is also fixed.

At the onset of fabrication, the quality of boards under inspection is in a fluid state and defects are more likely to occur, and for this reason, time must be taken to carry out pattern inspection in as much detail as possible at the onset of manufacturing. As the manufacturing process continues, the quality of boards under inspection stabilizes, and the occurrence of defects tends to decrease. Accordingly, increasing the size of resolution of pattern inspection, while slightly reducing inspection performance, yields the advantages of reduced inspection time as well as reduced inspection costs. However, as described hereinabove, the prior art suffers from the problem that resolution is fixed and does not admit easy alteration.

In addition, the pattern inspection device disclosed in Japanese Patent Laid-open No. 69777/92 has a drawback in that it necessitates means for extracting pattern edge as well as a standard printed wiring board judged to be a good article for extracting pattern edge or the mask film used for producing boards serving as the object of inspection, and has the additional drawback that it cannot handle cases in which defects critical to quality control occur unexpectedly in areas not inspected for defects.

SUMMARY OF THE INVENTION

The object of the present invention is to obtain data on defects through comparative inspection using standard data and to use statistics from a prescribed number of inspection results to control resolution so as to rationally shorten inspection time.

To achieve this object, the present invention provides a pattern inspecting device for printed wiring boards that includes:

image signal processing means for outputting as a digital image signal an optical image of a printed wiring board in which a conductive wiring pattern is formed on an insulating substrate;

image analyzing means for inspecting quality by comparing the digital image signal with standard inspection data of a prescribed resolution determined in advance and outputting detected defect data when defects are detected; and a confirmation station that judges whether defects indicated by the detected defect data are actual defects or detected defects that are not actually defects but have been outputted as defects, and outputs defect data distinguishing between actual defects and detected defects; and further includes inspection result processing means for recording to an inspection result data base the detected defects and actual defects outputted from the confirmation station, and judging whether or not quality of manufacture of printed wiring boards under inspection has stabilized referring detected defect data and actual defect data of the inspection results data base, correcting the resolution according to this judgment result, automatically preparing and outputting standard inspection data corresponding to the corrected resolution, and renewing said standard inspection data.

According to a preferable embodiment of the pattern inspecting device of the present invention, the image signal processing means includes an A/D converter that converts to a digital signal an image signal of a printed wiring board used for testing that is obtained using a prescribed camera and outputs the result, a binary circuit that converts the digital image signal to a binary image signal and outputs the result, and a preprocessing circuit that, following application of a compensating process to the binary image signal, converts the binary image signal to a digital image signal and outputs the result; the image analyzing means includes an image memory that temporarily stores the digital image signal outputted from the preprocessing circuit, a comparative inspection circuit that comparatively analyzes inputted digital image signal outputted from the preprocessing circuit and the standard inspection data stored the image memory and outputs inspection results, and a design rule check circuit that performs a design rule check of the inputted digital image signals outputted from the preprocessing circuit and outputs the result; the inspection result processing means includes an inspection result data base that stores detected defect and actual defect data outputted from the confirmation station, a statistical analysis circuit that statistically analyzes defect data stored in the inspection result data base, a resolution determination circuit that refers to the analysis results of the statistical analysis circuit and judges whether or not quality of manufacturing of printed wiring boards under testing has stabilized, and an inspection data generation circuit that receives the determination result when the resolution determination circuit determines that manufacturing quality of printed wiring boards under testing has stabilized, seeks standard inspection data within the data base of printed wiring board standard inspection data, appropriately corrects resolution set in the optical image data extraction, automatically produces and outputs standard inspection data based on the corrected resolution, thereby renewing the standard inspection data.

Furthermore, the pattern inspecting device of the present invention preferably includes means whereby the statistical analysis is performed for every 100 inspections.

The above and other objects, features, and advantages of the present invention will become apparent from the following description based on the accompanying drawings which illustrate an example of a preferred embodiment of the present invention.

DETAILED DESCRIPTION OF THE PREFERRED EMBODIMENTS

Embodiments of the present invention will next be explained with reference to the accompanying drawings.

Figure 1:
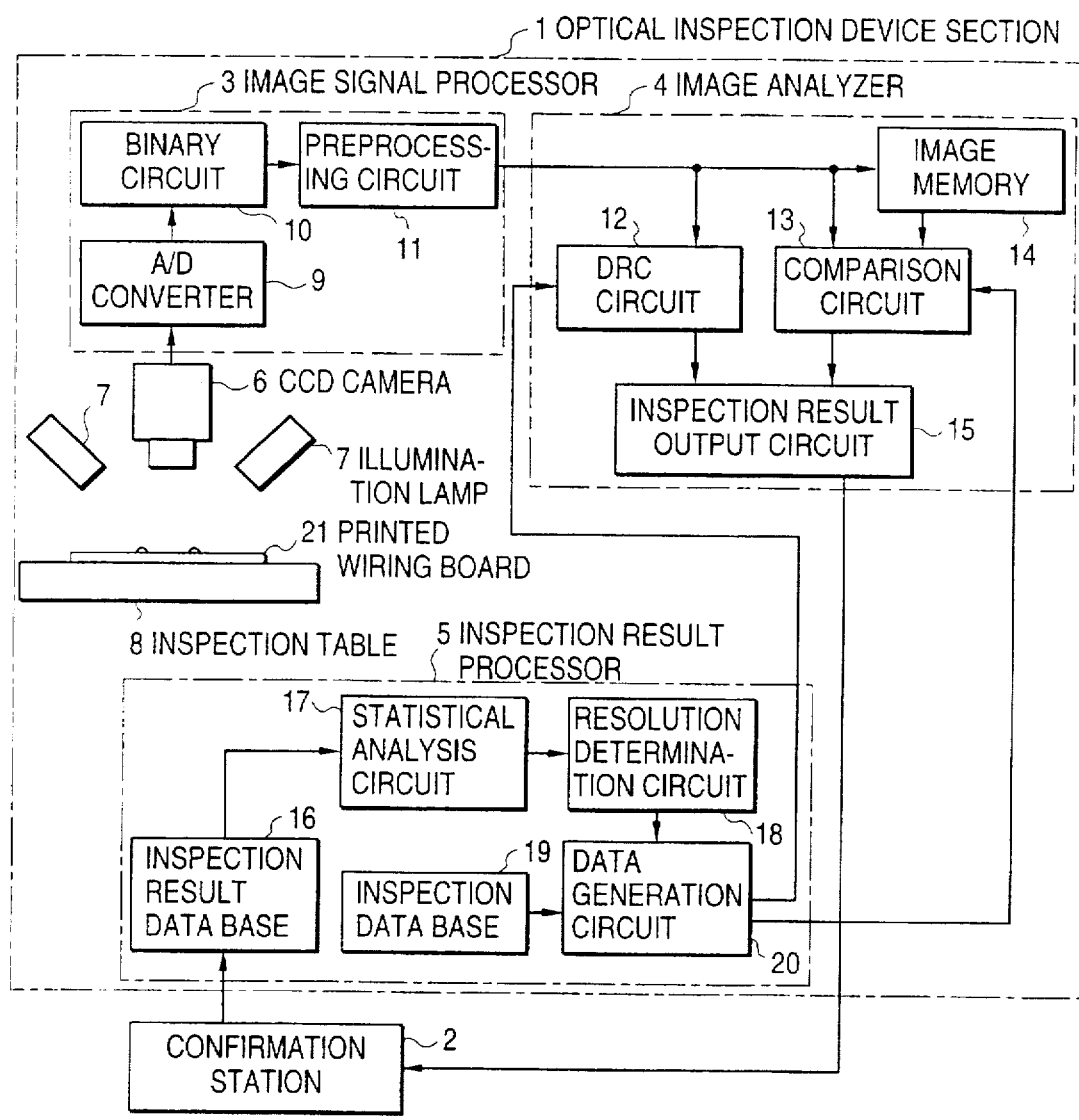
FIG. 1 is a block diagram showing the first embodiment of a pattern inspecting device according to the present invention.

FIG. 1 is a block diagram showing the first embodiment of a pattern inspecting device according to the present invention. This pattern inspecting device includes a confirmation station 2 and an optical inspection device section 1 that includes, for a printed wiring board 21 which is the object of inspection, an image signal processor 3, an image analyzer 4, an inspection result processor 5, a CCD camera 6, a pair of illumination lamps 7, and an inspection table 8. The image signal processor 3 is made up of an A/D converter 9, a binary circuit 10, and a preprocessing circuit 11. The image analyzer 4 is made up of a DRC circuit 12, a comparison circuit 13, an image memory 14, and an inspection result output circuit 15. The inspection result processor 5 is made up of an inspection result data base 16, a statistical analysis circuit 17, a resolution determination circuit 18, an inspection data base 19 and an inspection data generation circuit 20.

Figure 2:
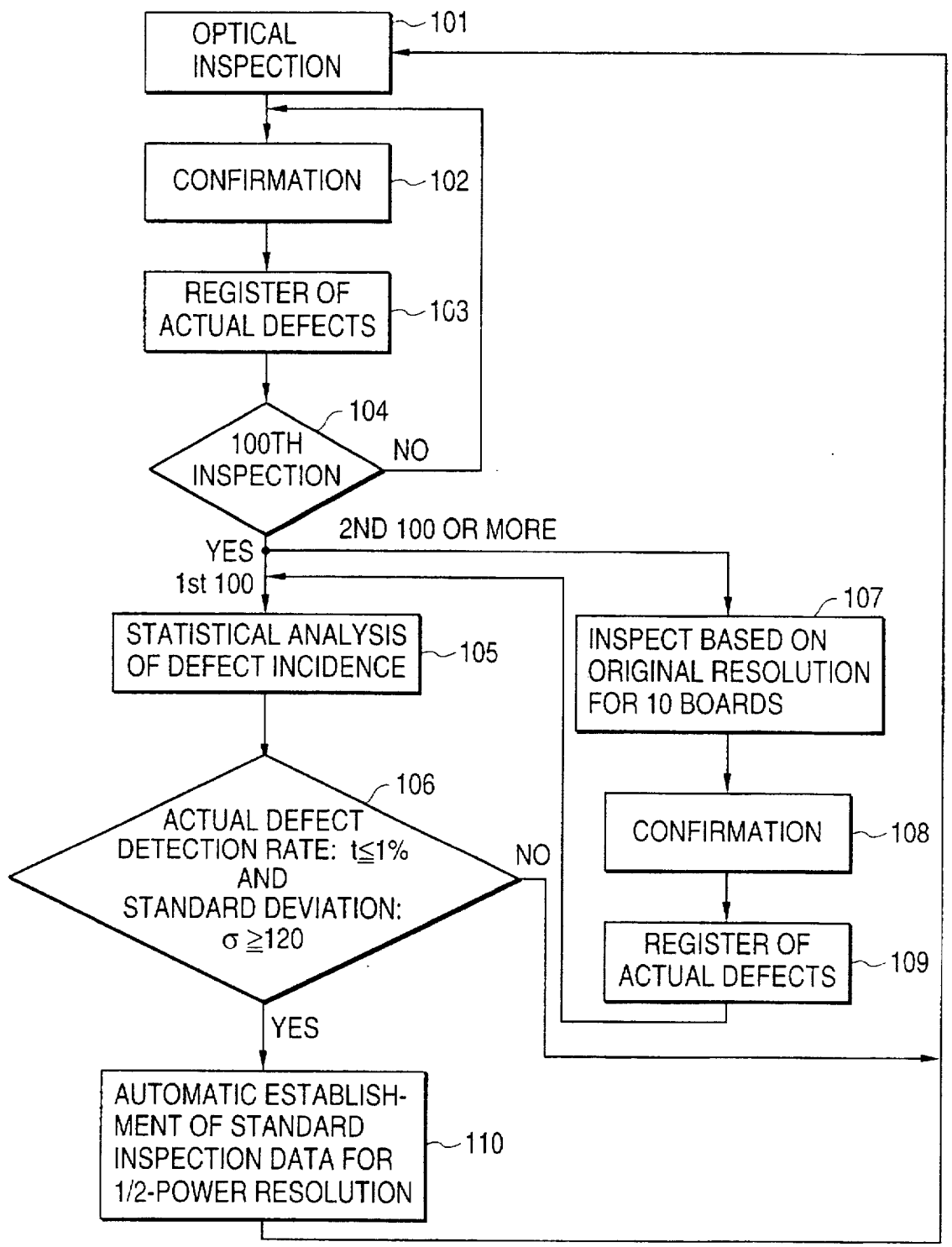
FIG. 2 is a flow chart of the first embodiment of a pattern inspecting device according to the present invention.

FIG. 2 is a flow chart showing the processing procedure of the pattern inspection method of the present invention.

The operation of the present embodiment will be explained hereinbelow with reference to FIG. 1 and FIG. 2.

The light projected by lamps 7 is directed toward printed wiring board 21, the object of inspection, and the projected light that is in turn reflected from printed wiring board 21 is captured by CCD camera 6. An image signal is outputted which is then converted to a digital image signal in A/D converter 9 and inputted to binary circuit 10, where it is converted to a binary signal. This binary signal is subjected to preprocessing in preprocessing circuit 11 that includes image compensation, after which it is outputted and sent to image analyzer 4. In image analyzer 4, the image signal that has undergone preprocessing is inputted to DRC circuit 12, comparative inspection circuit 13, and image memory 14, where the image signal is stored. In comparative inspection circuit 13, the image signal inputted from preprocessing circuit 11 is compared/analyzed with master data of the printed wiring board that is outputted from image memory 14, and the result of this comparative inspection is inputted to inspection result output circuit 15. A design rule check is performed upon the inputted image signal at DRC circuit 12, and the results of this inspection are inputted to inspection results output circuit 15. The inspection results from comparative inspection circuit 13 and DRC circuit 12 outputted from inspection result output circuit 15 are transmitted to confirmation station 2 (Step 101). These inspection results are confirmed at confirmation station 2 (Step 102). Here, detected defects found in the inspection results (which include items which are not actual defects but detected as defects in inspection) are judged to confirm as actual defects (items which are true defects) or not, distinguished between detected defects and actual defects, and inputted and registered in inspection result data base 16 (Step 103).

In this way, with each inspection of a printed wiring board 21, data including defects and actual defects detected by means of CCD camera 6, image signal processor 3, and image analyzer 4 are stored in inspection result data base 16. When carrying out the above-described inspection process on 100 printed wiring boards (Step 104), if this inspection completes the first 100 boards, data including defects and actual defects stored in inspection result data base 16 are inputted to statistical analysis circuit 17 and a statistical analysis is performed regarding the number of detected defects, the number of actual defects, and the distribution of incidence for the 100-printed wiring board lot (Step 105).

Through the above-described processing procedures, values for the actual defect detection rate (t) and standard deviation ($\sigma_x$, $\sigma_y$) given by the following formulae can be found for each inspection of 100 printed wiring boards 21:

(1) If t is the actual defect detection rate:

(2) Where all coordinates for actual defect coordinate values ($X_i$, $Y_i$) (i=1, 2, ... n).

Standard deviation of the X coordinate=$\sigma_x$

Standard deviation of the Y coordinate=$\sigma_y$

When receiving the results of statistical analysis, resolution determination circuit 18 determines whether or not the actual defect detection rate t is less than or equal to 1% (Condition A), and if the standard deviation $\sigma_x$ is equal to or greater than 120, and $\sigma_y$ is equal to or greater than 120 (Condition B) (Step 106).

At the outset of inspection of the printed wiring boards 21, the rate of incidence of actual defects t is high because manufacturing quality of printed wiring boards 21 is still in an unstable state, and in addition, the standard deviations $\sigma_x$ and $\sigma_y$ are both small because defects tend to occur in specific areas depending on the pattern formed on printed wiring boards 21. However, as processing of the printed wiring boards continues, the manufacturing quality of the printed wiring boards gradually stabilizes, the rate of incidence of actual defects t accordingly drops, and the values of standard deviations $\sigma_x$ and $\sigma_y$ both grow larger.

If a state (hereinbelow referred to as Condition C) is achieved wherein both of Condition A ($t \leq 1\%$) and Condition B ($\sigma_x \geq 120/\sigma_y \geq 120$) are satisfied as described hereinabove, it is determined at resolution determination circuit 18 that the manufacturing quality of printed wiring boards 21 has stabilized. This judgment result is received at inspection data generation circuit 20, whereupon inspection data base 19 is searched for inspection data of printed wiring boards 21, and new inspection data of lower resolution are automatically produced (Step 110). The resolution, i.e., pixel size, of inspection data is normally 7–12 $\mu m^2$, but the newly produced inspection data here has half the resolution of normal data, i.e., pixel size is 14–24 $\mu m^2$. Further, if Condition C is not satisfied in Step 106, optical inspection is continued at the original resolution (Step 101).

When the above-described Condition C is satisfied, the new inspection data are transferred to comparative inspection circuit 13 which is included within image analyzer 4. These inspection data are received at comparative inspection circuit 13, whereupon inspection including comparative analysis based on the new inspection data obtained using a pixel size of 14–24 $\mu m^2$ is performed as the optical inspection of printed wiring boards 21 (Step 101). As explained hereinabove, the recognition process of Step 102, the process of registering actual defects of Step 103, and the process of judging completion of inspecting 100 boards of Step 104 are each carried out, but when inspection of 100 printed wiring boards has been executed based on the above-described new inspection data (step 107), and inspection of the following ten printed boards is carried out based on inspection data obtained based on the original 1-power resolution (a pixel size of 7–12 $\mu m^2$). A confirmation process (Step 108) and an actual defect registering process (Step 109) similar to Steps 102 and Step 103, respectively, are next performed, following which the process switches over to Step 105, and a statistical analysis process is executed regarding the corresponding incidence of defects (Step 105). If judgment regarding Condition A is performed and Condition A is not satisfied, inspection is performed based on inspection data obtained from the original 1-power resolution. Subsequent processing procedures are carried out as described hereinabove.

As described above, the inspection of printed wiring boards 21 is continued through a process whereby inspection data are automatically reconsidered and approved upon completing inspection of each 100 printed wiring boards 21.

The present invention as described in the foregoing description performs a statistical analysis process based on the results of inspection upon completing inspection of each lot of 100 printed wiring boards, and by referring to these analysis results to automatically set the size per pixel, i.e., the value governing resolution at the time of optical inspection, to n times the original value, allows the inspection time required for image recognition as well as for extracting inspection results from obtained inspection data to be cut to 1/n-th, thereby providing the effect of improving the processing speed capacity of the pattern inspection device.

Furthermore, as a countermeasure against deterioration in quality due to variation occurring in the process of fabricating printed wiring boards, the employed inspection data are automatically reconsidered and verified upon completing inspection of each 100 printed wiring boards, and inspection is therefore conducted based on inspection data of differing resolutions appropriate to the quality conditions of the printed wiring boards under inspection with emphasis on the precision of defect detection. The present invention therefore provides the effects of maintaining the precision of defect detection according to the quality of printed wiring boards and sharply reducing the time required for inspection.

It is to be understood, however, that although the characteristics and advantages of the present invention have been set forth in the foregoing description, the disclosure is illustrative only, and changes may be made in the arrangement of the parts within the scope of the appended claims.

What is claimed is:

1. A pattern inspecting device for printed wiring boards, comprising:

image signal processing means for outputting a digital image signal after converting from an optical image of a printed wiring board in which a conductive wiring pattern is formed on an insulator substrate;

image analyzing means for inspecting quality by comparing said digital image signal with reference inspection data of a prescribed pixel resolution determined in advance and outputting detected defect data when defects are detected; and a confirmation station that judges whether defects indicated by said detected defect data are actual defects or detected defects that are not actually defects but have been outputted as defects, and outputs defect data distinguishing actual defects from detected defects; and inspection result processing means for recording detected defects and actual defects outputted from said confirmation station to an inspection result data base, judging whether quality of manufacture of printed wiring boards under inspection has stabilized based on a statistical analysis of a defect occurrence ratio by referring to detected defect data and actual defect data of the inspection results data base, adjusting said pixel resolution according to the result of said judging, automatically preparing and outputting a new reference inspection data corresponding to the adjusted pixel resolution, and renewing said reference inspection data.

2. A pattern inspecting device according to claim 1, wherein said image signal processing means comprises an A/D converter that converts an image signal of a printed wiring board which is obtained using a prescribed camera to a digital signal for testing and outputs the result, a binary circuit that converts said digital image signal to a binary image signal and outputs the result, and a preprocessing circuit that, follows a compensating process to said binary image signal, and converts the binary image signal to a digital image signal and outputs the result;

wherein said image analyzing means comprises an image memory that temporarily stores digital image signals outputted from said preprocessing circuit, a comparative inspection circuit that comparatively analyzes inputted digital image signals outputted from said preprocessing circuit and a just preceding digital image signal stored in said image memory and outputs inspection results, and a design rule check circuit that performs a design rule check of said inputted digital image signals outputted from said preprocessing circuit and outputs the result; and wherein said inspection result processing means comprises an inspection result data base that stores detected defect and actual defect data outputted from said confirmation station, a statistical analysis circuit that statistically analyzes defect data stored in the inspection result data base, a resolution determination circuit that refers to analysis results from said statistical analysis circuit and judges whether quality of manufacturing of printed wiring boards under testing has stabilized, and an inspection data generation circuit that receives said determination results when said resolution determination circuit determines that quality of manufacturing of printed wiring boards under testing has stabilized, searches reference inspection data of printed wiring board within the inspection result data base, appropriately adjusts the pixel resolution corresponding to said optical image, and automatically produces and outputs new reference inspection data based on the adjusted pixel resolution.

3. A pattern inspecting device according to claim 2, wherein said statistical analysis circuit performs a statistical analysis for every 100 inspections.

4. A pattern inspecting device for printed wiring boards, comprising:

an image signal processor that outputs a digital image signal converted from an optical image of a printed wiring board in which a conductive wiring pattern is formed on an insulator substrate;

an image analyzer that inspects for quality by comparing said digital image signal with reference inspection data of a prescribed pixel resolution determined in advance and outputs detected defect data when defects are detected;

a confirmation station that judges whether defects indicated by said detected defect data are actual defects or detected defects that are not actually defects but have been outputted as defects, and outputs defect data distinguishing actual defects from detected defects; and an inspection result processor that records detected defects and actual defects outputted from said confirmation station to an inspection result data base, judges whether quality of manufacture of printed wiring boards under inspection has stabilized based on a statistical analysis of a defect occurrence ratio by referring to detected defect data and actual defect data of the inspection results data base, adjusting said pixel resolution according to the result of said judging, automatically preparing and outputting a new reference inspection data corresponding to the adjusted pixel resolution, and renewing said reference inspection data.

* * * * *